US010132803B2

(12) United States Patent
Farrugia et al.

(10) Patent No.: US 10,132,803 B2
(45) Date of Patent: Nov. 20, 2018

(54) SULFONATED POLYESTER-METAL NANOPARTICLE COMPOSITE TONER FOR COLORIMETRIC SENSING APPLICATIONS

(71) Applicant: XEROX CORPORATION, Norwalk, CT (US)

(72) Inventors: Valerie M. Farrugia, Oakville (CA); Wendy Chi, Toronto (CA); Sandra J. Gardner, Oakville (CA)

(73) Assignee: XEROX CORPORATION, Norwalk, CT (US)

( * ) Notice: Subject to any disclaimer, the term of this patent is extended or adjusted under 35 U.S.C. 154(b) by 588 days.

(21) Appl. No.: 14/820,808

(22) Filed: Aug. 7, 2015

(65) Prior Publication Data

US 2017/0038376 A1 Feb. 9, 2017

(51) Int. Cl.
*G01N 33/543* (2006.01)
*G03G 9/08* (2006.01)

(52) U.S. Cl.
CPC ..... *G01N 33/54386* (2013.01); *G03G 9/0802* (2013.01); *G03G 9/0825* (2013.01); *G03G 9/0827* (2013.01)

(58) Field of Classification Search
CPC .................................................... G01N 33/543
See application file for complete search history.

(56) References Cited

U.S. PATENT DOCUMENTS

| | | | | |
|---|---|---|---|---|
| 5,491,094 | A | 2/1996 | Ramana et al. | |
| 5,593,807 | A | 1/1997 | Sacripante et al. | |
| 6,004,714 | A | 12/1999 | Ciccarelli et al. | |
| 6,020,101 | A * | 2/2000 | Sacripante ......... | G03G 9/08755 430/110.2 |
| 7,214,504 | B2 | 5/2007 | Anaokar et al. | |
| 2003/0211035 | A1* | 11/2003 | Burns .................. | A61K 41/009 424/1.11 |
| 2004/0137352 | A1 | 7/2004 | McStravick et al. | |
| 2012/0202148 | A1* | 8/2012 | Veregin ................. | G03G 9/093 430/108.1 |
| 2014/0220608 | A1 | 8/2014 | Andreescu et al. | |

FOREIGN PATENT DOCUMENTS

| | | |
|---|---|---|
| CA | 2585816 | 4/2006 |
| CA | 2812312 | 11/2012 |
| CN | 100510704 | 7/2009 |

OTHER PUBLICATIONS

Foreign Patents Retrieval System (FPRS on EAST), Abstract, Equivalent of Hui et al. (CN100510704, IDS sumitted Aug. 7, 2015), published Jul. 8, 2009 (Year: 2009).*

(Continued)

*Primary Examiner* — Tracy Vivlemore
*Assistant Examiner* — Nam P Nguyen
(74) *Attorney, Agent, or Firm* — Pillsbury Winthrop Shaw Pittman LLP

(57) ABSTRACT

A toner composite material includes toner particles that include a sulfonated polyester and a wax and metal nanoparticles disposed on the surface of the toner particles. A method includes providing such toner composite materials, fusing the material to a substrate and covalently linking a ligand to the surface of the silver nanoparticles via a thiol, carboxylate, or amine functional group. Detection strips include a substrate and such toner composite materials fused on the substrate.

3 Claims, 12 Drawing Sheets

(56) References Cited

OTHER PUBLICATIONS

Chattopadhyay, D. P. et al., Preparation, Characterization and Stabiization of Nanosized Copper Particles, Int. J. Pure Appl. Sci. Technol., 9(1):1-8 (2012).

Wei Yu et al., Synthesis and Characterization of Monodispersed Copper Colloids in Polar Solvents, Nanoscale Res. Lett. 4:465-470 (2009).

Dominguez-Gonzalez, R., L. González Varela, and P. Bermejo-Barrera. "Functionalized gold nanoparticles for the detection of arsenic in water." Talanta 118 (2014): 262-269.

Zeljka Krpetic et al., Importance of Nanoparticle Size in Colorimetric and SERS-Based Multimodal Trace Detection of Ni(II) Ions with Functional Gold Nanoparticles, Small 8(5):707-714 (2012).

Chih-Ching Huang, Chang Huan-Tsung. 2007. "Parameters for selective colorimetric sensing of mercury(II) in aqueous solutions using mercaptopropionic acid-modified gold nanoparticles." Chemical communications (Cambridge, England) (12): 1215-7.

Fang Chai et al. Colorimetric Detection of Pb2+ Using Glutathione Functionalized Gold Nanoparticles ACS Appl. Mater. Interfaces 2:1466-1470(2010).

Yu-Rong Ma et al. Colorimetric detection of copper ions in tap water during the synthetix of silver/dopamine nanoparticles, Chem. Commun. 47:12643-12645(2011).

Cuiping Han et al. Highly selective and sensitive colorimetric probes for Yb3+ ions based on supramolecular aggregates assembled from β-cyclodextrin-4,4'-dipyridine inclusion complex modified silver nanoparticles, Chem. Commun. 24:3545-3547 (2009).

Ningning Yang et al. A new rapid colorimetric detection method of Al3+ with high sensitivity and excellent selectivity based on a new mechanishm of aggregation of smaller etched silver nanoparticles, Talanta 122:272-277 (2014).

Karuvath Yoosaf et al. 2007 In situ synthesis of metal nanoparticles and selective naked-eye detection of lead ions from aqueous media. J. Phys. Chem. C 111 (34), 12839-12847.

Vaibhavkumar N. Mehta et al. Dopamine dithiocarbamate functionalized silver nanoparticles as colorimetric sensors for the detection of cobalt ion, Anal. Methods 5:1818-1822 (2013).

Ke Cao et al. Phenylboronic acid modified silver nanoparticles for colorimetric dynamic analysis of glucose, Biosensors and Bioelectronics 52:188-195 (2014).

Haibing Li et al. Synthesis of aza-crown ether-modified silver nanoparticles as colorimetric sensors for Ba2+ Supramol. Chem. 22:544-547 (2010).

Ren-Der Jean et al. Functionalized Silica Nanoparticles by Nanometallic Ag Decoration for Optical Sensing of Organic Molecule, J. Phys. Chem. 114:15633-15639 (2010).

Haibing Li et al. Highly sensitive and selective tryptophan colorimetric sensor based on 4,4-biperidine-functionalized silver nanoparticles, Sens. Actuators B 145:194-199 (2010).

Diana Vilela, Maria Cristina González, and Alberto Escarpa. Sensing colorimetric approaches based on gold and silver nanoparticles aggregation: chemical creativity behind the assay. A review. Analytica chimica acta 751 (2012): 24-43.

R. A. Sperling, et al. , Surface Modification, Functionalization and Bioconjugation of Colloidal Inorganic Nanoparticles, Philosophical Transactions of the Royal Society A: Mathematical, Physical and Engineering Sciences 368.1915: 1333-1383 (2010).

* cited by examiner

SULFONATED POLYESTER-METAL NANOPARTICLE COMPOSITE TONER FOR COLORIMETRIC SENSING APPLICATIONS

BACKGROUND

The present disclosure relates to colorimetric detection. In particular, the present disclosure relates to the use of printable composite materials for colorimetric sensing applications.

There is a continuing need for simple, rapid and inexpensive point-of-collection detection assays for a variety of applications such as monitoring of food and water for toxic contaminants, diagnostic applications, and environmental analysis. Such assays are particularly useful in the developing world where expensive instrumentation and/or specialized expertise for standard sample analysis are prohibitive. These assays would also have the benefit of reducing the time and costs associated with sample transportation and storage as well as providing the convenience of immediate results for rapid decisions on-the-spot (e.g., detection of blood alcohol content through the point-of-collection Breathalyzer test allowing a police officer to arrest an individual immediately).

Colorimetric assays are one form of point-of-collection testing that is rapid, inexpensive and requires little to no training or instrumentation to perform. Colorimetric test strips are currently on the market for a variety of applications such as pH measurement, measurement of blood glucose and triglycerides (see, for example, U.S. Pat. No. 7,214,504, which is incorporated herein by reference in its entirety), albumin measurement in urine (see for example, Canadian Patent Application No. 2,585,816, which is incorporated herein by reference in its entirety) and analysis of free chlorine (see for example, U.S. Pat. No. 5,491,094, which is incorporated herein by reference in its entirety). In some forms, the technology behind these strips is largely based on existing colorimetric indicator molecules such as Coomassie Blue for albumin. Such molecules may be of limited utility and are not universal for any analyte of interest. Alternatively, some strips are based on enzymatic reactions (e.g., lipoprotein lipase and 4-aminoantipyridine for triglyceride detection) which require the production of purified proteins, making manufacture costly to scale-up.

An emerging class of colorimetric assays utilizes surface plasmon resonance (SPR) of nanoparticles as the source of color change to report the presence of a target analyte (see e.g., U.S. Patent Application No. 2014/0220608, Canadian Patent Application No. 2,812,312, and Chinese Patent Application No. 100510704). However, only a small portion of these assays are provided in a paper-based test strip.

SUMMARY

In some aspects embodiments herein relate to toner composite materials comprising toner particles comprising a sulfonated polyester, and a wax and the toner composites further comprising metal nanoparticles disposed on the surface of the toner particles.

In some aspects embodiments herein relate to methods comprising providing a toner composite material comprising toner particles comprising a sulfonated polyester, and silver nanoparticles disposed on the surface of the toner particle, the method further comprising fusing the toner composite material to a substrate and covalently linking a ligand to the surface of the silver nanoparticles via a thiol, carboxylate, or amine functional group.

In some aspects embodiments herein relate to detection strips comprising a substrate and a toner composite material fused on the substrate; the toner composite material comprising toner particles comprising a sulfonated polyester and silver nanoparticles disposed on the surface of the toner particle.

BRIEF DESCRIPTION OF DRAWINGS

Various embodiments of the present disclosure will be described herein below with reference to the figures wherein.

DETAILED DESCRIPTION

Figure 1:
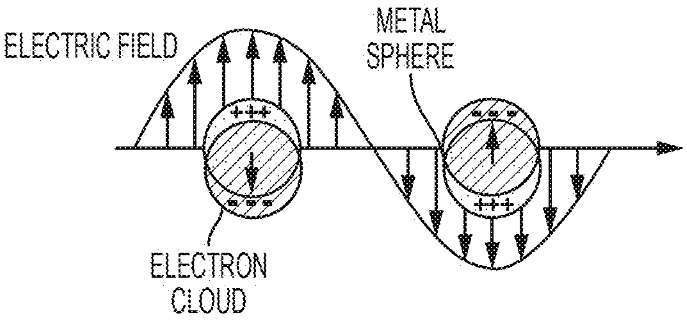
FIG. 1 shows electrons oscillating in surface plasmon resonance (SPR).

Embodiments herein provide printable colorimetric materials based on branched sulfonated polyester (BSPE) toner particles with silver nanoparticles disposed on the toner particle surface. These materials retain their colorimetric sensing properties even after being fused to a paper substrate and can be customized to detect a variety of analytes through surface functionalization of the silver nanoparticles with one or more small molecule ligands designed to interact with one or more target analytes. Such printable materials are simple to use and cost-effective in producing colorimetric test strips for a variety of sensing applications. Because the material is printable, multiple analytes can be simultaneously screened in a spatially addressable array on a single test strip.

Silver (and gold nanoparticles) sensing systems have the advantage of being customizable for a variety of analytes through the ligands that are used to functionalize the nanoparticles. Specificity of these systems can be tailored by using multiple ligands recognizing the same analyte. Domínguez-González et al., Talanta 118:262-269 (2014). Colorimetric sensing systems for various molecules can be created through the chemical synthesis of a ligand with specificity for any query molecule, provided that it has a thiol group or other means of chemical attachment it to the silver (or other metal) nanoparticle surface.

An advantage of silver nanoparticles compared to ionic silver, in particular when bound to a larger particle, sediment, colloidal particle, or macromolecule is that the silver nanoparticles are not water soluble, and will not be freely released into the environment.

The compositions and methods herein enable customizable digitally printed colorimetric test strips with the benefit of being biodegradable. Other conventional EA styrene-acrylate type toners typically do not benefit from such biodegradability.

In embodiments, there are provided toner composite materials comprising toner particles comprising a sulfonated polyester and metal nanoparticles disposed on the surface of the toner particles wherein the toner particles further comprise a wax.

In embodiments, the sulfonated polyester is a branched polymer. In embodiments, the sulfonated polyester is a copolymer. Specific examples of sulfonated polyesters that can be used in the methods disclosed herein include, but are not limited to, the hydrogen, ammonium, alkali or alkali earth metals such as lithium, sodium, potassium, cesium, magnesium, barium, iron, copper, vanadium, cobalt, calcium salts of: random copoly(ethylene-terephthalate)-copoly-(ethylene-5-sulfo-isophthalate), copoly(propylene-terephthalate)-copoly-(propylene-5-sulfo-isophthalate), copoly(diethylene-terephthalate)-copoly-(diethylene-5-sulfo-isophthalate), copoly(propylene-diethylene-terephthalate)-copoly (propylene-diethylene-5-sulfo-isophthalate), copoly(propylene-butylene-terephthalate)-copoly-(propylene-butylene-5-sulfo-isophthalate), copoly-(propoxylated bisphenol-A-fumarate)-copoly(propoxylated bisphenol A-5-sulfo-isophthalate), copoly (ethoxylated bisphenol-A-fumarate)-copoly(ethoxylated bisphenol A-5-sulfo-isophthalate), copoly(ethoxylated bisphenol-A-maleate)-copoly (ethoxylated bisphenol A-5-sulfo-isophthalate), mixtures thereof and the like, The sulfonated portion of the copolymer may be present in an amount of, for example, from about 0.5 to about 8 mole percent of the resin, or about 0.5 to about 6 mole, or about 1.0 to about 5 mole.

For the aforementioned sulfonated polyester resins, the glass transition temperature can be selected to be from about 45° C. to about 65° C. as measured by the Differential Scanning Calorimeter (DSC), the number average molecular weight can be selected to be from about 1,000 grams per mole to about 200,000 grams per mole. In embodiments, the sulfonated polyester has a number average molecular weight in a range from about 1,000 to about 100,000, or from about 2,000 to about 50,000. In embodiments, the sulfonated polyester has a number average molecular weight in a range from about 2,000 grams per mole to about 200,000 grams per mole, or about 2,000 to about 150,000, or about 2,000 to 100,000.

In embodiments, the weight average molecular weight can be selected to be from about 2,000 grams per mole to about 200,000 grams per mole as measured by the Gel Permeation Chromatography (GPC), or about 2,000 to about 150,000, or about 2,000 to 100,000 and the polydispersity can be selected to be from about 1.6 to about 100 as calculated by the ratio of the weight average to number average molecular weight.

In embodiments, the metal nanoparticles are silver (0) or gold (0), or copper (0). For Cu (0), see *Int J. Pure Appl. Sci. Technol.,* 9(1):1-8 (2012); *Nanoscale Res. Lett.* 4:465-470 (2009) In embodiments, the metal nanoparticles have an effective diameter in a range from about 1 nm to about 1000 nm, or about 1 nm to about 500 nm, or about 1 nm to about 100 nm.

In embodiments, the toner composite material further comprises a ligand linked to the surface of the metal nanoparticles, the ligand being linked to the surface of the metal nanoparticles by an organic functional group selected from the group consisting of a thiol, a carboxylate, and an amine. In embodiments, the ligand is selected to bind to a target analyte of interest. Exemplary ligands include, without limitation, Au nanoparticles (Au NP) modified with nitrilotriacetic acid (NTA) with and I-carnosine (Krpetic et al., *Small* 8(5):707-714 (2012)), mercaptopropionic acid-modified Au NPs (Chih-Ching Huang et al. *Chem. Commun.* 12:1215-1217 (2007)), glutathione-stabilized Au NPs (Fang Chai et al *ACS Appl. Mater. Interfaces* 2:1466-1470(2010)), silver/dopamine nanoparticles (Yu-rong Ma et al *Chem. Commun.* 47:12643-12645(2011)), beta-cyclodextrin-4,4'-dipyridine supramolecular inclusion complex-modified AgNPs (Han, C et al. *Chem. Commun.* 24:3545-3547 (2009)), AgNPs stabilized by reduced glutathione in the presence of L-cysteine (Ningning Yang et al. *Talanta* 122: 272-277 (2014)), AgNPs or AuNPs with gallic acid (Karuvath Yoosaf et al. *J. Phys. Chem. C,* 111(34): 12839-12847 (2007)), dopamine dithiocarbamate functionalized AgNPs (Vaibhavkumar N. Mehta et al. *Anal. Methods* 5:1818-1822 (2013)), phenylboronic acid modified AgNPs (Ke Cao et al. *Biosensors and Bioelectronics* 52:188-195 (2014)), Aza-crown ether-AgNPs (Haibing Li et al. *Supramol. Chem.* 22:544-547 (2010)), label-free AgNPs (Ren-Der Jean et al. *J. Phys. Chem.* 114:15633-15639 (2010)) and bipyridine-AgNPs (Haibing Li et al. *Sens. Actuators B* 145:194-199 (2010)). Those skilled in the art will recognize that the foregoing are merely exemplary and that any known ligand-analyte pairing can be adapted in accordance with the embodiments disclosed herein.

The aforementioned ligands may be used to detect analytes such as Ni(II) ions, Hg(II) ions, Pb(II) ions, Cu(II) ions, Yb(III) ions, Al(III), Pb(II) ions, Co(II) ions, glucose, Ba(II) ions, melamine and tryptophan.

In embodiments, the toner composite material is fused on a substrate. In particular the substrate is a test strip, such as a paper test strip. That is the toner composite being made from toner material allows for printing on a substrate, typically paper for ease of manufacture and low cost test strips, for example.

In embodiments, there are provided methods comprising providing a toner composite material comprising toner particles comprising a sulfonated polyester and silver nanoparticles disposed on the surface of the toner particle fusing the toner composite material to a substrate, and covalently linking a ligand to the surface of the silver nanoparticles via a thiol, carboxylate, or amine functional group.

In embodiments, the covalent linking step is performed after the fusing step. In embodiments, the covalent linking step is performed before the fusing step.

In embodiments, the fusing step is performed in a spatially defined area of the substrate via printing. In embodiments, multiple ligands are covalently linked to the surface of the silver nanoparticles in a spatially defined arrangement, thereby providing a functionalized substrate capable of being used to detect multiple analytes.

In embodiments, there are provided detection strips comprising a substrate and a toner composite material fused on the substrate; the toner composite material comprising toner particles comprising a sulfonated polyester and silver nanoparticles disposed on the surface of the toner particle.

In embodiments, the detection strip further comprises a ligand covalently linked to the surface of the silver nanoparticles via a thiol, carboxylate, or amine functional group, the ligand selected to detect a target analyte. In embodiments, the detection strip is configured with multiple ligands that are spatially addressed, thereby allowing for simultaneous detection of multiple target analytes.

In embodiments, the substrate is paper. Any suitable substrate or recording sheet can be employed, including plain papers such as XEROX 4200 papers, XEROX Image Series papers, Courtland 4024 DP paper, ruled notebook paper, bond paper, silica coated papers such as Sharp Company silica coated paper, JuJo paper, HAMMERMILL LASERPRINT paper, and the like, glossy coated papers such as XEROX Digital Color Elite Gloss, Sappi Warren Papers LUSTROGLOSS, specialty papers such as Xerox DURAPAPER, and the like, transparency materials, fabrics, textile products, plastics, polymeric films, inorganic recording mediums such as metals and wood, and the like, transparency materials, fabrics, textile products, plastics, polymeric films, inorganic substrates such as metals and wood, and the like. For simple detection strips, paper-based substrates may be particularly suitable.

The BSPE toner particles can be manufactured for specific colorimetric sensing applications with the goal of producing paper-based detection strips similar to pH paper for colorimetric sensing of various analytes of interest. Some specific examples of analytes that are commonly regulated by government authorities and of interest for color strip detection include, without limitation, copper, arsenic, melamine, aluminum, chromium and various pesticides. The silver-nanoparticle impregnated BSPE toner particles can be sold in cartridges allowing an end user to select their own specific downstream detection application downstream of printing onto detection strips.

In one exemplary embodiment, BSPE toner particles were prepared from the emulsion aggregation of BSPE, followed by reduction of $Ag^{+}$ ions onto the BSPE toner particle surface to form silver nanoparticles disposed on the surface of the toner particles. The Examples herein below evaluate these particles for colorimetric properties both in emulsion form and after fusing to a paper substrate. A process to prepare microparticles from sulfonated polyesters in non-functional xerographic applications (is disclosed in U.S. Pat. No. 5,593,807, which is incorporated herein by reference in its entirety. This process generates toner particles of narrow size distribution and controllable particle size. The aggregating agents used are generally divalent ions such as zinc acetate and magnesium chloride salts. The particle morphology can be easily controlled via temperature, time and stirring to provide toner particles that are potato-shaped or completely spherical, and a continuum of morphologies in between.

The method of synthesizing silver nanoparticles (AgNPs) after aggregation of metal sulfonated polyester particles in water is an environmentally friendly method because no solvents are necessary. The localization of AgNPs on the surface of the toner particle allows them to interact with the surrounding environment while simultaneously preventing excessive leaching of silver ions from the material. The reducing agent used to generate nanoparticulate silver also diffuses throughout the polyester matrix and fosters the formation of well-dispersed AgNPs on the surface of the BSPE toner particles.

Silver nanoparticles are known for their unique optical properties relative to ionic and bulk silver. Surface plasmon resonance is one such optical property and occurs when the conductive electrons of metal nanoparticles oscillate collectively at the same frequency as incident electromagnetic radiation (see FIG. 1). As a result there is a strong absorption of light at certain wavelengths which gives the silver nanoparticles a bright coloration that changes with differing nanoparticle size and shape, inter-nanoparticle distance and the refractive index of the surrounding medium. Vilela, et al. Analytica chimica acta 751:24-43 (2012).

Figure 2:
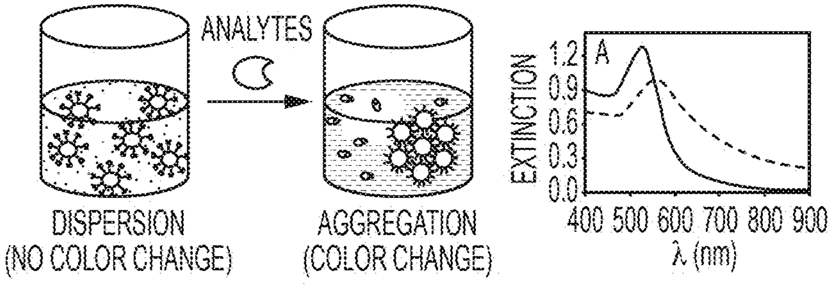
FIG. 2 shows nanoparticle surface plasmon resonance for colorimetric sensing.

In accordance with embodiments herein, because the color of colloidal nanosilver depends on the distance between individual nanoparticles, the BSPE-AgNP system disclosed herein can be used as a colorimetric sensor for a variety of analytes (FIG. 2). To do so, the surface of the silver nanoparticles can be functionalized with a small molecule ligand that binds specifically to an analyte of interest. This functionalization can be established via a thiol linking group on the ligand which can form a covalent bond with the surface of the silver nanoparticle. Other functional groups such as carboxyl and amine groups can also perform this function. See, for example, Sperling, et al. Philosophical Transactions of the Royal Society A: Mathematical, Physical and Engineering Sciences 368.1915: 1333-1383 (2010). When a target analyte is added to a ligand-functionalized silver nanoparticle, the analyte can bind and aggregate, which in turn results in a color change which can be quantified by measuring the change in absorption at various wavelengths via UV-VIS spectroscopy.

Embodiments herein provide emulsion aggregation (EA) toner based on BSPE and further comprising silver nanoparticles disposed on the surface of the BSPE toner particles. The resultant BSPE toner particles are used for colorimetric sensing applications. The BSPE toner particles can be used to conduct customizable, digitized colorimetric printing for a variety of analytes. Some specific examples of applications are monitoring drinking water for harmful metals (copper, cadmium, chromium, arsenic), analyzing bodily fluids for diagnostic purposes (glucose, triglyercides, disease markers) and screening food products for chemical contaminants such as melamine in infant formula.

In embodiments there are provided nanocomposites comprising nanoparticulate silver disposed on the surface of sulfonated polyester particles which particles are suitable for use as toner.

In embodiments, there are provided methods for preparing such nanocomposites as EA toner particles comprising silver nanoparticles disposed thereon, the method comprising: (1) dispersing a sulfonated polyester resin in water while heating it at about 90° C.; (2) aggregating the dispersed sulfonated polyester by adding an aqueous solution of zinc acetate dropwise while heating from about 55° C. to 60° C. to form toner particles; (3) adding an aqueous solution of silver nitrate dropwise to the toner particles after the desired particle size is reached to form silver ion impregnated toner particles, and (4) adding an aqueous solution of a reducing agent dropwise to the silver ion impregnated toner particles thus forming silver nanoparticle-BSPE nanocomposite toner particles of the desired diameter. The size of the growing polyester aggregates in step (2) can be monitored throughout the process to determine when a target diameter has been obtained. Rate of growth and circularity can be modulated by adjusting the rate of zinc acetate addition, temperature and stirring rate. In embodiments, the toner particles have a circularity in a range from 0.930 to 0.990, or 0.950 to 0.980, or 0.960 to 0.980.

In accordance with the Examples below the nanocomposite sulfonated polyester toners comprising silver nanoparticles can be used for colorimetric sensing application for a variety of analytes, such as $Cu^{2+}$, dopamine, and glucose while the nanocomposite material is present as an emulsion. As a proof-of-concept it was shown that the toner retains colorimetric function for $Cu^{2+}$ when modified with L-cysteine after being fused to a filter paper substrate. Thus, the material can be adapted for printing and forming detection strips.

Other toner components may also be included in the toner particles, as described herein below.

In some embodiments, toner particles may comprise a wax. Suitable waxes for the present toner particles include, but are not limited to, alkylene waxes such as alkylene wax having about 1 to about 25 carbon atoms, polyethylene, polypropylene or mixtures thereof. The wax is present, for example, in an amount of about 6% to about 15% by weight based upon the total weight of the composition. Examples of waxes include those as illustrated herein, such as those of the aforementioned co-pending applications, polypropylenes and polyethylenes commercially available from Allied Chemical and Petrolite Corporation, wax emulsions available from Michaelman Inc. and the Daniels Products Company, EPOLENE N-15™ commercially available from Eastman Chemical Products, Inc., VISCOL 550-P™, a low weight average molecular weight polypropylene available from Sanyo Kasei K.K., and similar materials. The commercially available polyethylenes possess, it is believed, a molecular weight (Mw) of about 1,000 to about 5,000, and the commercially available polypropylenes are believed to possess a molecular weight of about 4,000 to about 10,000. Examples of functionalized waxes include amines, amides, for example Aqua SUPERSLIP 6550™, SUPERSLIP 6530™ available from Micro Powder Inc., fluorinated waxes, for example POLYFLUO 190™, POLYFLUO 200™, POLYFLUO 523XF™, AQUA POLYFLUO 41™, AQUA POLYSILK 19™, POLYSILK 14™ available from Micro Powder Inc., mixed fluorinated, amide waxes, for example Microspersion 19™ also available from Micro Powder Inc., imides, esters, quaternary amines, carboxylic acids or acrylic polymer emulsion, for example JONCRYL 74™, 89™, 130™, 537™, and 538™, all available from SC Johnson Wax, chlorinated polypropylenes and polyethylenes available from Allied Chemical and Petrolite Corporation and SC Johnson Wax.

In some embodiments, the wax comprises a wax in the form of a dispersion comprising, for example, a wax having a particle diameter of about 100 nanometers to about 500 nanometers, water, and an anionic surfactant. In embodiments, the wax is included in amounts such as about 6 to about 15 weight percent. In embodiments, the wax comprises polyethylene wax particles, such as Polywax 850, commercially available from Baker Petrolite, although not limited thereto, having a particle diameter in the range of about 100 to about 500 nanometers, although not limited. The surfactant used to disperse the wax is an anionic surfactant, although not limited thereto, such as, for example, NEOGEN RK™ commercially available from Kao Corporation or TAYCAPOWER BN2060 commercially available from Tayca Corporation.

In embodiments, other surface toner additives may be included. For example, the toner particles disclosed herein can include an externally applied additive which includes at least one of surface-treated silica, surface-treated titania, spacer particles, and combinations thereof. The additives may be packaged together as an additives package to add to the toner particles. That is, the toner particles are first formed, followed by mixing of the toner particles with the materials of the additives package. The result is that some components of the additive package may coat or adhere to external surfaces of the toner particles, rather than being incorporated into the bulk of the toner particles.

Any suitable untreated silica or surface treated silica can be used. Such silicas can be used alone, as only one silica, or can be used in combination, such as two or more silicas. Where two or more silicas are used in combination, it is may be beneficial, although not required, that one of the surface treated silicas be a decyl trimethoxysilane (DTMS) surface treated silica. In particular embodiments, the silica of the decyl trimethoxysilane (DTMS) surface treated silica may be a fumed silica.

Conventional surface treated silica materials are known and include, for example, TS-530 from Cabosil Corporation, with an 8 nanometer particle size and a surface treatment of hexamethyldisilazane; NAX50, obtained from Evonik Industries/Nippon Aerosil Corporation, coated with HMDS; H2050EP, obtained from Wacker Chemie, coated with an amino functionalized organopolysiloxane; CAB-O-SIL® fumed silicas such as for example TG-709F, TG-308F, TG-810G, TG-811F, TG-822F, TG-824F, TG-826F, TG-828F or TG-829F with a surface area from 105 to 280 m2/g obtained from Cabot Corporation; and the like. Such conventional surface treated silicas are applied to the toner surface for toner flow, triboelectric charge enhancement, admix control, improved development and transfer stability, and higher toner blocking temperature.

In other embodiments, other surface treated silicas can also be used. For example, a silica surface treated with polydimethylsiloxane (PDMS), can also be used. Specific examples of suitable PDMS-surface treated silicas include, for example, but are not limited to, RY50, NY50, RY200, RY200S and R202, all available from Nippon Aerosil, and the like.

In embodiments, the silica additive is a surface-treated silica. When so provided, the surface treated silica may be the only surface treated silica present in the toner composition. As described below, the additive package may also beneficially include large-sized sol-gel silica particles as spacer particles, which is distinguished from the surface treated silica described herein. Alternatively, for example where small amounts of other surface treated silicas are introduced into the toner composition for other purposes, such as to assist toner particle classification and separation, the surface treated silica is the only xerographically active surface treated silica present in the toner composition. Any other incidentally present silica thus does not significantly affect any of the xerographic printing properties. In some embodiments, the surface treated silica is the only surface treated silica present in the additive package applied to the toner composition. Other suitable silica materials are described in, for example, U.S. Pat. No. 6,004,714, the entire disclosure of which is incorporated herein by reference.

In some embodiments, the silica additive may be present in an amount of from about 1 to about 4 percent by weight, based on a weight of the toner particles without the additive or, in an amount of from about 0.5 to about 5 parts by weight additive per 100 parts by weight toner particle or from about 1.6 weight percent to about 2.8 weight percent or from about 1.5 or from about 1.8 to about 2.8 or to about 3 percent by weight.

In some embodiments, the silica has an average particle size of from about 10 to about 60 nm, or from about 15 to about 55 nm, or from about 20 to about 50 nm.

Another component of an additive package may include a titania, and in embodiments a surface treated titania. In embodiments, the surface treated titania used in embodiments is a hydrophobic surface treated titania.

Conventional surface treated titania materials are known and include, for example, metal oxides such as TiO2, for example MT-3103 from Tayca Corp. with a 16 nanometer particle size and a surface treatment of decylsilane; SMT5103, obtained from Tayca Corporation, comprised of a crystalline titanium dioxide core MT500B coated with DTMS; P-25 from Degussa Chemicals with no surface treatment; an isobutyltrimethoxysilane (i-BTMS) treated hydrophobic titania obtained from Titan Kogyo Kabushiki Kaisha (IK Inabata America Corporation, New York); and the like. Such surface treated titania are applied to the toner surface for improved relative humidity (RH) stability, triboelectric charge control and improved development and transfer stability.

While any of the conventional and available titania materials can be used, it may be beneficial that specific surface treated titania materials be used, which have been found to unexpectedly provide superior performance results in toner particles. Thus, while any of the surface treated titania may be used in the additive package, in some embodiments the material may be a "large" surface treated titania (i.e., one having an average particle size of from about 30 to about 50 nm, or from about 35 to about 45 nm, particularly about 40 nm). In particular, it has been found that the surface treated titania provides one or more of better cohesion stability of the toners after aging in the toner housing, and higher toner conductivity, which increases the ability of the system to dissipate charge patches on the toner surface.

Specific examples of suitable surface treated titanias include, for example, but are not limited to, an isobutyltrimethoxysilane (i-BTMS) treated hydrophobic titania obtained from Titan Kogyo Kabushiki Kaisha (IK Inabata America Corporation, New York); SMT5103, obtained from Tayca Corporation or Evonik Industries, comprised of a crystalline titanium dioxide core MT500B coated with DTMS (decyltrimethoxysilane); and the like. The decyltrimethoxysilane (DTMS) treated titania is particularly beneficial, in some embodiments.

In embodiments, only one titania, such as surface treated titania, is present in the toner composition. That is, in some embodiments, only one kind of surface treated titania is present, rather than a mixture of two or more different surface treated titanias.

The titania additive may be present in an amount of from about 0.5 to about 4 percent by weight, based on a weight of the toner particles without the additive, or about 0.5 to about 2.5, or about 0.5 to about 1.5, or about 2.5 or to about 3 percent by weight. In some embodiments, the surface-treated titania has an average particle size of from about 10 to about 60 nm, or from about 20 to about 50 nm, such as about 40 nm.

Another component of the additive package may include a spacer particle. In embodiments, the spacer particles have an average particle size of from about 100 to about 150 nm. In some embodiments, the spacer particles are selected from the group consisting of latex particles, polymer particles, and sol-gel silica particles. In some embodiments, the spacer particle used in embodiments is a sol-gel silica.

Spacer particles, particularly latex or polymer spacer particles, are described in, for example, U.S. Patent Application Publication No. 2004/0137352, the entire disclosure of which is incorporated herein by reference.

In some embodiments, the spacer particles are comprised of latex particles. Any suitable latex particles may be used without limitation. As examples, the latex particles may include rubber, acrylic, styrene acrylic, polyacrylic, fluoride, or polyester latexes. These latexes may be copolymers or crosslinked polymers. Specific examples include acrylic, styrene acrylic and fluoride latexes from Nippon Paint (e.g. FS-101, FS-102, FS-104, FS-201, FS-401, FS-451, FS-501, FS-701, MG-151 and MG-152) with particle diameters in the range from 45 to 550 nm, and glass transition temperatures in the range from 65° C. to 102° C.

These latex particles may be derived by any conventional method in the art. Suitable polymerization methods may include, for example, emulsion polymerization, suspension polymerization and dispersion polymerization, each of which is well known to those versed in the art. Depending on the preparation method, the latex particles may have a very narrow size distribution or a broad size distribution. In the latter case, the latex particles prepared may be classified so that the latex particles obtained have the appropriate size to act as spacers as discussed above. Commercially available latex particles from Nippon Paint have very narrow size distributions and do not require post-processing classification (although such is not prohibited if desired).

In a further embodiment, the spacer particles may also comprise polymer particles. Any type of polymer may be used to form the spacer particles of this embodiment. For example, the polymer may be polymethyl methacrylate (PMMA), e.g., 150 nm MP1451 or 300 nm MP116 from Soken Chemical Engineering Co., Ltd. with molecular weights between 500 and 1500K and a glass transition temperature onset at 120° C., fluorinated PMMA, KYNAR® (polyvinylidene fluoride), e.g., 300 nm from Pennwalt, polytetrafluoroethylene (PTFE), e.g., 300 nm L2 from Daikin, or melamine, e.g., 300 nm EPOSTAR-S® from Nippon Shokubai.

In embodiments, the spacer particles on the surfaces of the toner particles are believed to function to reduce toner cohesion, stabilize the toner transfer efficiency and reduce/minimize development falloff characteristics associated with toner aging such as, for example, triboelectric charging characteristics and charge through. These additive particles function as spacers between the toner particles and carrier particles and hence reduce the impaction of smaller conventional toner external surface additives, such as the above-described silica and titania, during aging in the development housing. The spacers thus stabilize developers against disadvantageous burial of conventional smaller sized toner additives by the development housing during the imaging process in the development system. The spacer particles function as a spacer-type barrier, and therefore the smaller toner additives are shielded from contact forces that have a tendency to embed them in the surface of the toner particles. The spacer particles thus provide a barrier and reduce the burial of smaller sized toner external surface additives, thereby rendering a developer with improved flow stability and hence excellent development and transfer stability during copying/printing in xerographic imaging processes. The toner compositions of the present disclosure thereby exhibit an improved ability to maintain their DMA (developed mass per area on a photoreceptor), their TMA (transferred mass per area from a photoreceptor) and acceptable triboelectric charging characteristics and admix performance for an extended number of imaging cycles.

The spacer particles may be present in an amount of from about 0.3 to about 2.5 percent by weight, based on a weight of the toner particles without the additive, or from about 0.6 to about 1.8, or from about 0.5 to about 1.8 percent by weight.

In some embodiments, the spacer particles are large sized silica particles. Thus, in some embodiments, the spacer particles have an average particle size greater than an average particles size of the silica and titania materials, discussed above. For example, the spacer particles in this embodiment are sol-gel silicas. Examples of such sol-gel silicas include, for example, X24, a 120 nm sol-gel silica surface treated with hexamethyldisilazane, available from Shin-Etsu Chemical Co., Ltd. In some embodiments, the spacer particles may have an average particle size of from about 60 to about 300 nm, or from about 75 to about 205 nm, such as from about 100 nm to about 150 nm.

In some embodiments, toner particles disclosed herein may be formed in the presence of surfactants. For example, surfactants may be present in a range of from about 0.01 to about 20, or about 0.1 to about 15 weight percent of the reaction mixture. Suitable surfactants include, for example, nonionic surfactants such as dialkylphenoxypoly-(ethyleneoxy) ethanol, available from Rhone-Poulenc as IGEPAL CA-210™, IGEPAL CA-520™, IGEPAL CA-720™, IGEPAL CO-890™, IGEPAL CO-720™, IGEPAL CO-290™, IGEPAL CA-210™, ANTAROX 890™ and ANTAROX 897™. In some embodiments, an effective concentration of the nonionic surfactant may be in a range of from about 0.01 percent to about 10 percent by weight, or about 0.1 percent to about 5 percent by weight of the reaction mixture.

Suitable anionic surfactants may include, without limitation sodium dodecylsulfate (SDS), sodium dodecylbenzene sulfonate, sodium dodecylnaphthalene sulfate, dialkyl benzenealkyl, sulfates and sulfonates, adipic acid, available from Aldrich, NEOGEN R™, NEOGEN SC™, available from Kao, Dowfax 2A1 (hexa decyldiphenyloxide disulfonate) and the like, among others. For example, an effective concentration of the anionic surfactant generally employed is, for example, about 0.01 percent to about 10 percent by weight, or about 0.1 percent to about 5 percent by weight of the reaction mixture In some embodiments, anionic surfactants may be used in conjunction with bases to modulate the pH and hence ionize the aggregate particles thereby providing stability and preventing the aggregates from growing in size. Such bases can be selected from sodium hydroxide, potassium hydroxide, ammonium hydroxide, cesium hydroxide and the like, among others.

Examples of additional surfactants, which may be added optionally to the aggregate suspension prior to or during the coalescence to, for example, prevent the aggregates from growing in size, or for stabilizing the aggregate size, with increasing temperature can be selected from anionic surfactants such as sodium dodecylbenzene sulfonate, sodium dodecylnaphthalene sulfate, dialkyl benzenealkyl, sulfates and sulfonates, adipic acid, available from Aldrich, NEOGEN R™, NEOGEN SC™ available from Kao, and the like, among others. These surfactants can also be selected from nonionic surfactants such as polyvinyl alcohol, polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxypoly(ethyleneoxy) ethanol, available from Rhone-Poulenac as IGEPAL CA-210™, IGEPAL CA-520™, IGEPAL CA-720™, IGEPAL CO-890™, IGEPAL CO-720™, IGEPAL CO-290™, IGEPAL CA-210™, ANTAROX 890™ and ANTAROX 897™. For example, an effective amount of the anionic or nonionic surfactant generally employed as an aggregate size stabilization agent is, for example, about 0.01 percent to about 10 percent or about 0.1 percent to about 5 percent, by weight of the reaction mixture.

In some embodiments acids that may be utilized in conjunction with surfactants to modulate pH. Acid may include, for example, nitric acid, sulfuric acid, hydrochloric acid, acetic acid, citric acid, trifluoroacetic acid, succinic acid, salicylic acid and the like, and which acids are in embodiments utilized in a diluted form in the range of about 0.5 to about 10 weight percent by weight of water or in the range of about 0.7 to about 5 weight percent by weight of water.

In some embodiments, toner particles disclosed herein may comprise a coagulant. In some embodiments, the coagulants used in the present process comprise polymetal halides, such as polyaluminum chloride (PAC) or polyaluminum sulfo silicate (PASS). For example, the coagulants provide a final toner having a metal content of, for example, about 400 to about 10,000 parts per million. In another feature, the coagulant comprises a poly aluminum chloride providing a final toner having an aluminum content of about 400 to about 10,000 parts per million.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 25° C.

Figure 3:
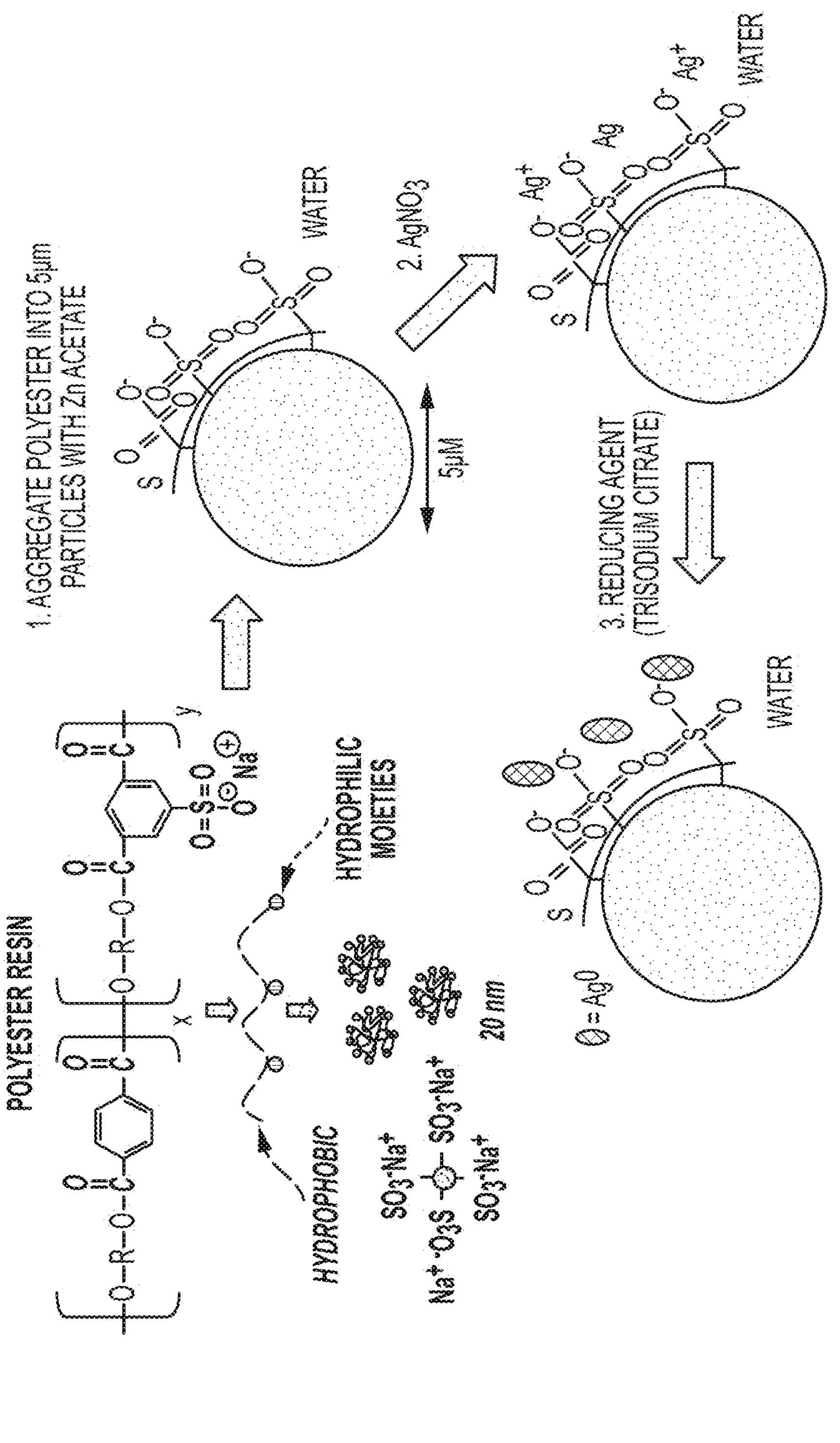
FIG. 3 shows a schematic representation of toner preparation.

The exemplary BSPE-silver nanoparticle composites described in the Examples below are based on emulsion/aggregation (EA) toner and were prepared via environmentally friendly methodology. After dispersing the polymer in water at about 90° C., the self-assembled BSPE nanoparticles were aggregated at about 56° C. with zinc acetate. After reaching the desired particle size of about 5 microns, $Ag^+$ ions were added and reduced onto the surface of the toner particles using citrate, as seen in FIG. 3. The sulfonated polyester can serve as both a carrier for the silver(I) ions and an organic matrix/stabilizer for the in situ synthesis of silver nanoparticles. The sulfonated polyester matrix also serves to inhibit the agglomeration of AgNPs.

Example 1

12.5% BSPE toner with 1% silver per weight of BSPE reduced onto the surface (Sample 1).

Figure 4A:
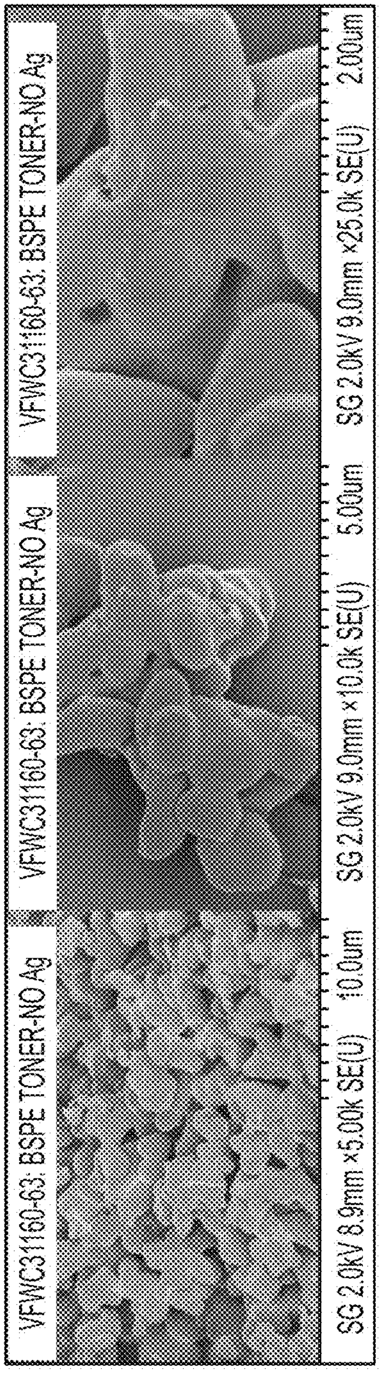
FIGS. 4A, 4B show scanning electron microscopy images of an exemplary BSPE toner with silver reduced onto the surface FIG. 4B compared to a control sample taken from the same reaction prior to silver addition FIG. 4A.
Figure 4B:
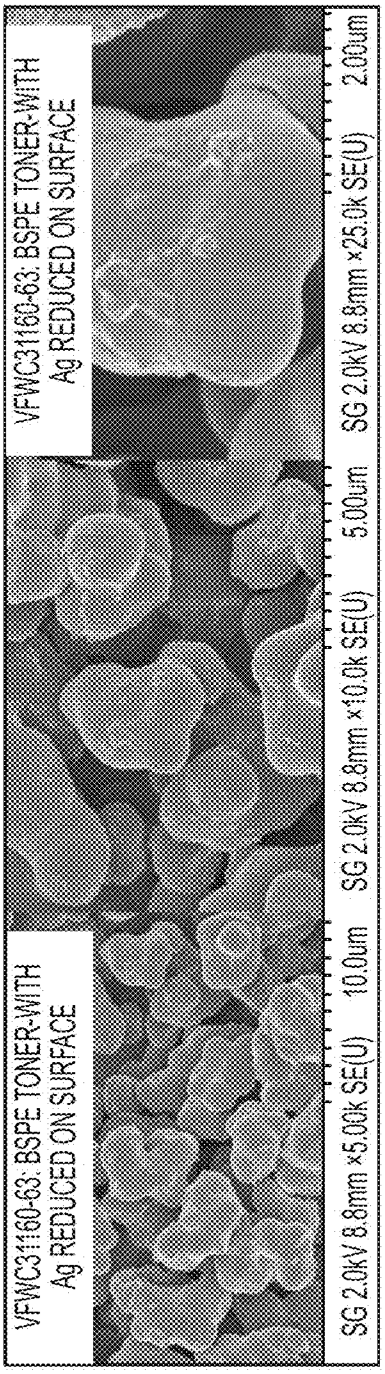
Figure 5:
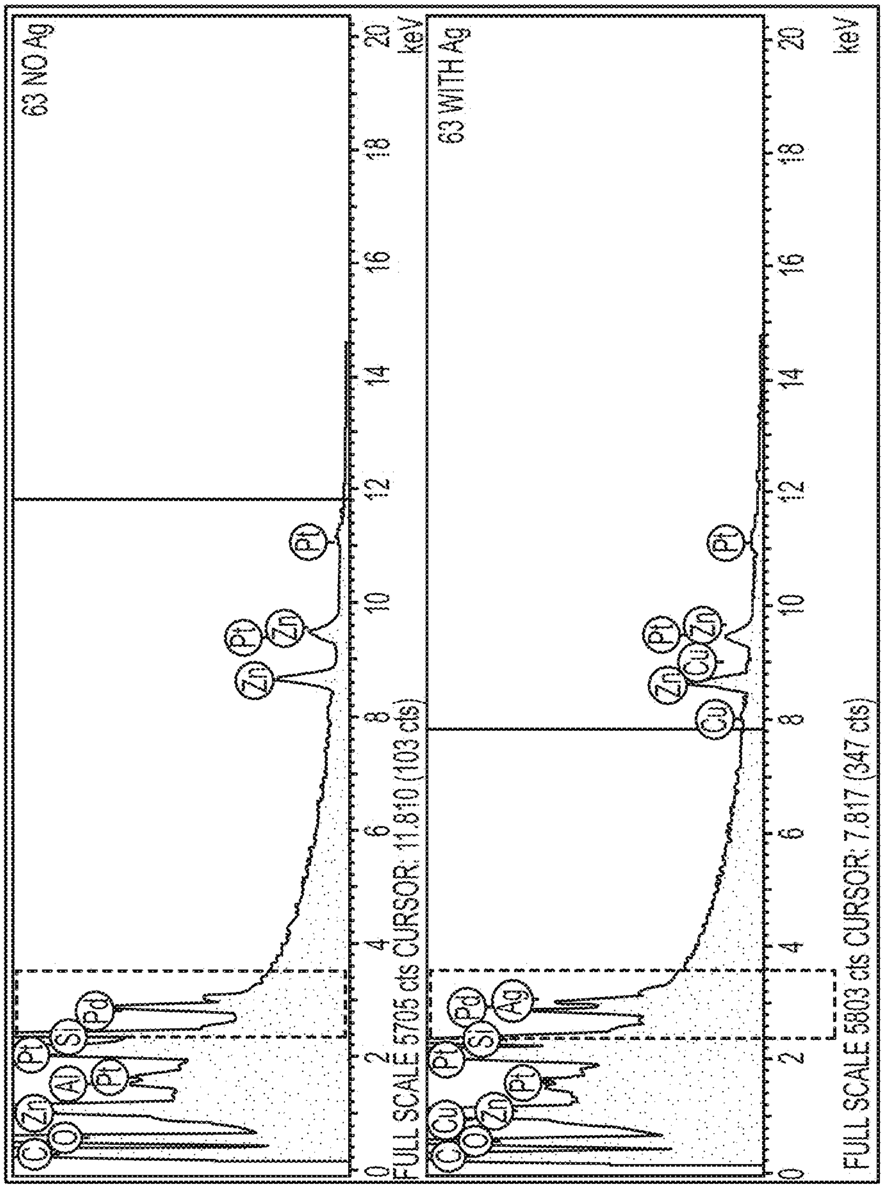
FIG. 5 shows an energy-dispersive X-ray spectroscopy (EDS) sum spectra of the exemplary BSPE toner of FIG. 4 prior to silver addition (top) and after silver reduction (bottom).

The reaction was carried out in a 3-necked, 500 mL round bottom flask equipped with an overhead stirrer, reflux condenser, thermocouple and electric heating mantle. 400 g of 12.5% BSPE emulsion was added to the flask and heated to 56° C. while stirring at 250 revolutions per minute (RPM). 6.0 g of zinc acetate dissolved in 120 g DIW was then added to the system using a pump (Fluid Metering Inc.) at a rate of 1.4 mL/min. Zinc acetate addition was complete after three hours at which point the particle size ($D_{50}$) as measured by the Nanotrac was 2.63 microns (RPM=190). The reactor continued to be heated at 56° C. for an hour, at which point the particle size measured by the Coulter Counter was 4.73 microns with a geometric size distributions by volume (GSDv) of 1.29 and a geometric size distributions by number (GSDn) of 1.35. The mean circularity of the particles as measured by the FPIA-3000 was 0.885. 0.5 g of $AgNO_3$ (1% wt per BSPE) dissolved in 25 mL de-ionized water (DIW) was added to the reactor at a rate of approx. 1.0 mL/min (RPM=190). The solution became pink. After 28 minutes 30 mL of 1% (w/w %) trisodium citrate solution (reducing agent) was added to the system at a rate of approx. 1.2 mL/min (RPM=190). Upon complete addition, the solution was allowed to cool overnight to room temperature (RPM=190) after which it was passed through a 25 micron sieve. The final appearance of the emulsion was a pink opaque solution. The solids content of the emulsion was 8.68%, the $D_{50}$ was 5.146 microns, and the zeta potential was −57.1 mV with a zeta deviation of 5.40 mV (breadth of distribution). Silver content as determined by inductively coupled plasma (ICP) was 5327 ppm. Energy Dispersive X-ray Spectroscopy-Scanning Electron Microscope (EDS-SEM) analysis confirmed the presence of silver on the surface of the toner particles compared to a control sample taken from the same reaction prior to silver addition (FIG. 4 and FIG. 5).

Example 2

Colorimetric Detection of Various Analytes Using Sample 1 in Emulsion

BSPE toner particles with silver reduced on the surface (Sample 1 from Example 1) was functionalized with ligands and tested against various analytes according to Table 1.

Example 3

6.25% BSPE toner with 4% silver per weight of BSPE reduced onto the surface (Sample 2).

Figures 7A, 7B:
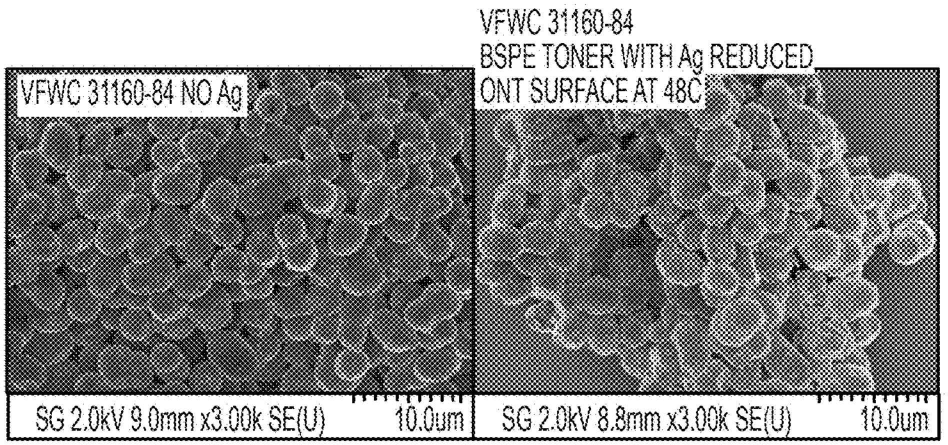
FIGS. 7A, 7B, 7C, 7D show scanning electron microscopy images of BSPE toner with silver reduced onto the surface FIG. 7B compared to a control sample taken from the same reaction prior to silver addition FIG. 7A. EDS confirmed that the deposits on the surface of the toner contain silver FIG. 7C, FIG. 7D.
Figures 7C, 7D:
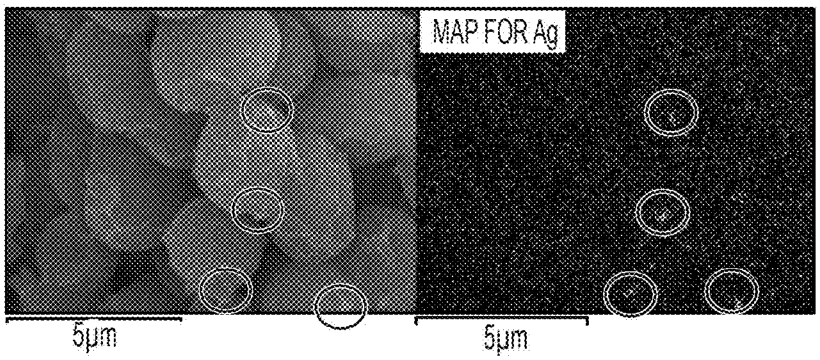
Figure 8:
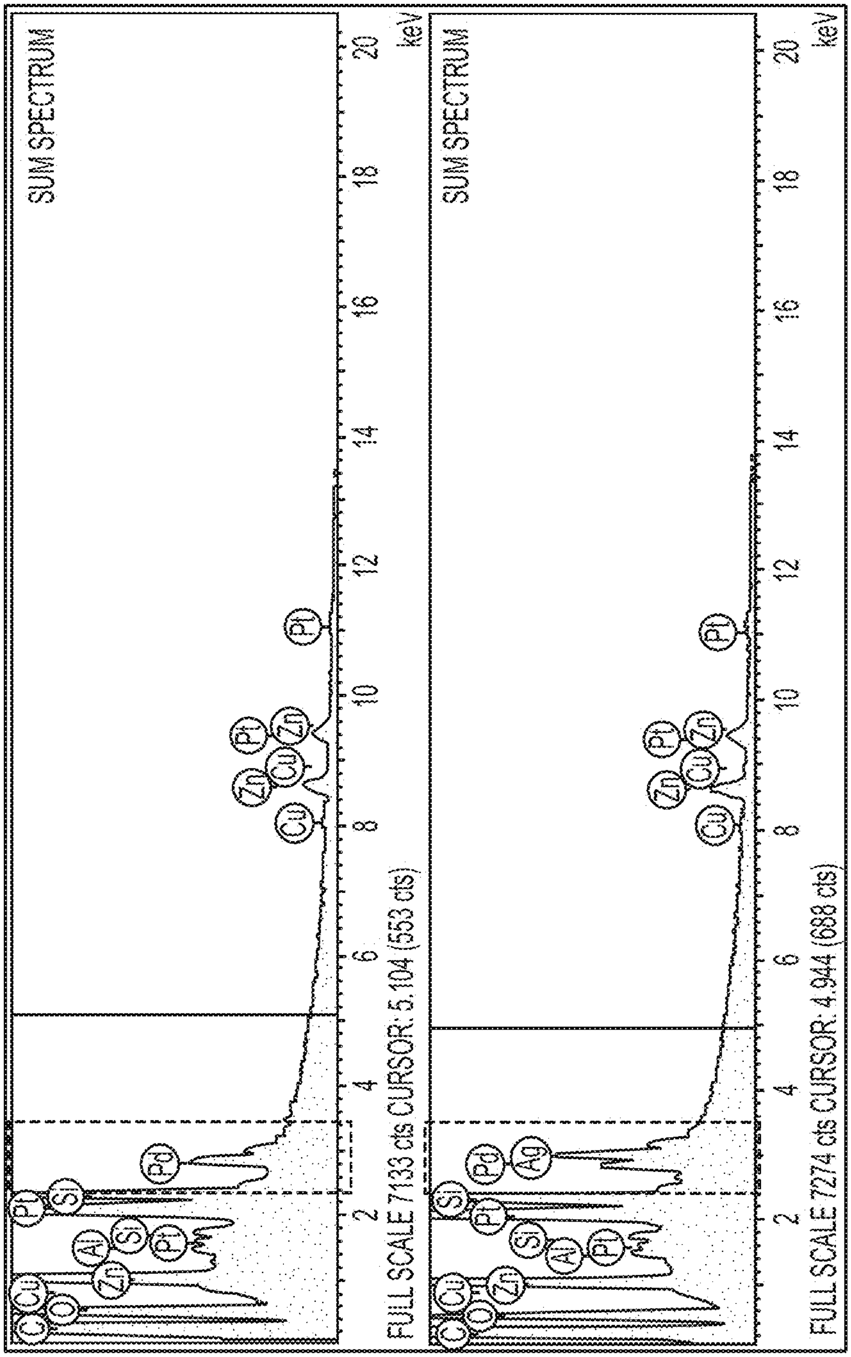
FIG. 8 shows EDS sum spectra of BSPE toner prior to silver addition (top) and after silver reduction (bottom).

The reaction was carried out in a 3 necked, 500 mL round bottom flask equipped with an overhead stirrer, reflux condenser, thermocouple and electric heating mantle. 100.0 g of 12.5% BSPE emulsion and 100.0 g of DIW were added to the flask and heated to 56° C. while stirring at 300 RPM. 1.5 g of zinc acetate dissolved in 30.0 g DIW was then added to the system using a FMI pump at a rate of 0.7 mL/min. Zinc acetate addition was complete after two hours at which point the particle size (D50) as measured by the Nanotrac was 1.913 microns. The reactor continued to be heated at 56° C. over the course of 3 days while the particle size was monitored hourly using the Nanotrac for $D_{50}<2$ microns and the Beckman Coulter Counter for $D_{50}>2$ microns. Stir rate was gradually reduced to 140 RPM to accelerate particle growth. After 1080 hours the particle size measured by the Coulter Counter was 4.353 microns with a GSDv of 1.16384 and a GSDn of 1.16999. The mean circularity of the particles as measured by the FPIA-3000 was 0.948. The temperature was reduced to 48° C. and 0.5 g of $AgNO_3$ (4% wt per BSPE) dissolved in 50.0 mL DIW was added to the reactor at a rate of approx. 0.5 mL/min (RPM=300). The solution became slightly pink. After 2 hours 30 mL of 1% (w/w %) trisodium citrate solution (reducing agent) was added to the system at a rate of approx. 0.4 mL/min (RPM=300). Upon complete addition, the solution was allowed to cool overnight to room temperature (RPM=180) after which it was passed through a 25 micron sieve. The final appearance of the emulsion was a light pink opaque solution. The solids content of the emulsion was 3.48%, the D50 was 4.353 microns, and the zeta potential was −57.3 mV with a zeta deviation of 4.86 mV (breadth of distribution). EDS-SEM confirmed the presence of silver on the surface of the toner particles compared to a control sample taken from the same reaction prior to silver addition (FIG. 7 and FIG. 8).

TABLE 1

| Analyte | Ligand | Functionalization method | Volume Functionalized Toner Added (mL) | Volume Analyte Added (mL) | Conc. of Analyte Added (mM) | Final Analyte Conc. (mM) | pH adjustment |
|---|---|---|---|---|---|---|---|
| $Cu^{2+}$ | L-cysteine | 3:1 volume of 10 mM cysteine added to toner immediately before testing | 1 | 2 | 40, 20, 10, 5, 3, 1, 0.5 | 13.3, 6.7, 3.3, 1.7, 1.0, 0.3, 0.2 | None |
| Dopamine | None | N/A | 1 | 2 | 1, 0.1, 0.01 | 0.67, 0.067, 0.0067 | Incr. (pH 11) |
| Glucose | 4-carboxyphenyl-boronic acid (4-CPBA) | 5:1 volume of 5 mM 4-CPBA added to toner and stirred for 1 hour at 200 RPM | 6 | 3 | 20, 5, 1, 0.1 | 6.67, 1.67, 0.33, 0.03 | Incr. (pH 11) |

Figure 6A:
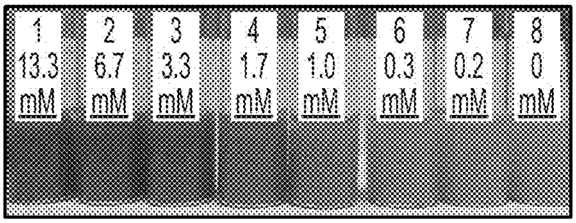
FIGS. 6A, 6B, 6C show images of BSPE toner with Ag reduced onto the surface Sample 1 (FIG. 4) used to detect FIG. 6A $Cu^{2+}$ ions through L-cysteine functionalization FIG. 6B dopamine with unfunctionalized toner and FIG. 6C glucose through 4-CPBA functionalization. Concentrations indicated are final analyte concentrations in FIG. 6A and concentrations of analytes added in FIG. 6B and FIG. 6C. Images taken immediately after analyte addition for FIG. 6A and 2 days after analyte addition for FIG. 6B and FIG. 6C.
Figure 6B:
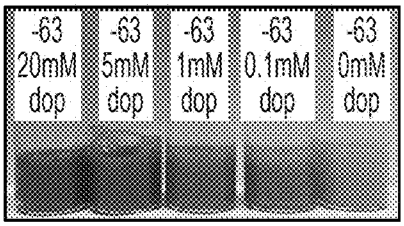
Figure 6C:
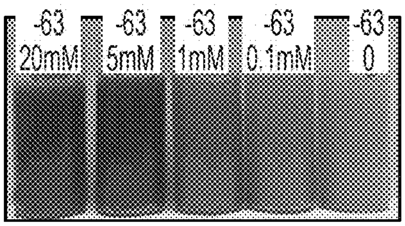

Results of colorimetric detection tests using Sample 1 in emulsion are shown in FIG. 6. Color change occurred immediately for $Cu^{2+}$ and after two days for dopamine and glucose. The dopamine and glucose samples required pH adjustment to approximately 11 using 1M NaOH for the color change to occur. A distinct color gradient from beige to dark brown for $Cu^{2+}$ and glucose and beige to dark silver for dopamine can be seen with increasing concentration of analyte, showing that the BSPE toner particle functions as a colorimetric sensor.

As shown in the SEM images in FIG. 7, the toner particles have a smooth appearance prior to silver reduction. After silver and reducing agent are added, the toner particles have bright deposits that correspond to Ag based on EDS, indicating the presence of silver nanoparticles on the surface of the toner.

The EDS sum spectra in FIG. 8 demonstrate that silver is not detected in the sample taken prior to silver reduction but is present after the reduction.

Example 4

Preparation of wet-deposition colorimetric toner samples for $Cu^{2+}$ detection: Sample 2 was diluted 4× in 10 mM L-cysteine and passed through Whatman 6 qualitative filter paper (cat no. 1006 125) pretreated with 1.0M NaOH through a cup with an exposed surface area of 9.62 cm2. The amount of toner passed through the filter was varied to adjust the toner mass area (TMA). The retained particles and filter paper were dried at room temperature, then enveloped in Mylar film and passed through a GBC laminator set to 80° C.

Example 5

Colorimetric detection of $Cu^{2+}$ using Sample 2 toner fused onto filter paper prepared in Example 4: Fused filters were cut into slices and dipped into 10 mM, 1 mM, 0.5 mM, 0.1 mM, 0.05 mM solutions of CuSO4 and dH2O. Filters were allowed to dry prior to being read on the Gretag Spectrolino for CIE L*a*b* and Spectrum Reflectance measurements. (NOTE—CIE L*a*b* (CIELAB) is a color space specified by the International Commission on Illumination (French Commission internationale de l'éclairage, hence its CIE initialism). It describes all the colors visible to the human eye and was created to serve as a device-independent model to be used as a reference.

Figure 9A:
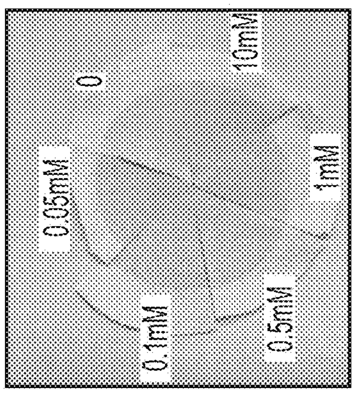
FIGS. 9A, 9B, 9C show scans of SAMPLE 2 toner functionalized with L-cysteine deposited at a TMA of FIG. 9A 1 mg/cm$^2$ FIG. 9B 2 mg/cm$^2$ and FIG. 9C 3 mg/cm$^2$ after dipping in indicated concentrations of $CuSO_4$.
Figure 9B:
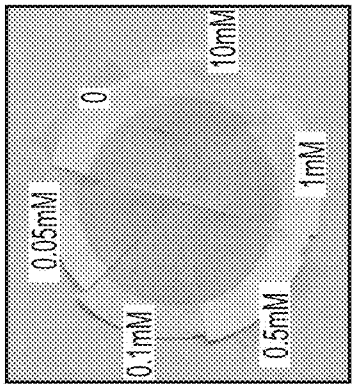
Figure 9C:
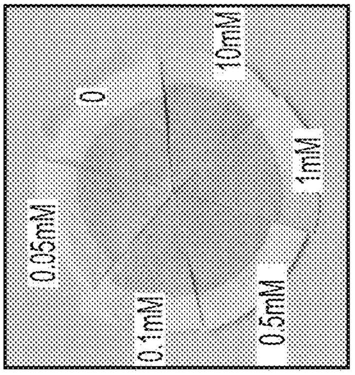

Color change in the filters dipped into $CuSO_4$ could be observed with the naked eye (FIG. 9). Toner not exposed to $Cu^{2+}$ retained a bright pink color which gradually changed to yellow with increasing concentrations of $Cu^{2+}$. This is most visible in the toner deposited at 1 mg/$cm^2$.

Figure 10:
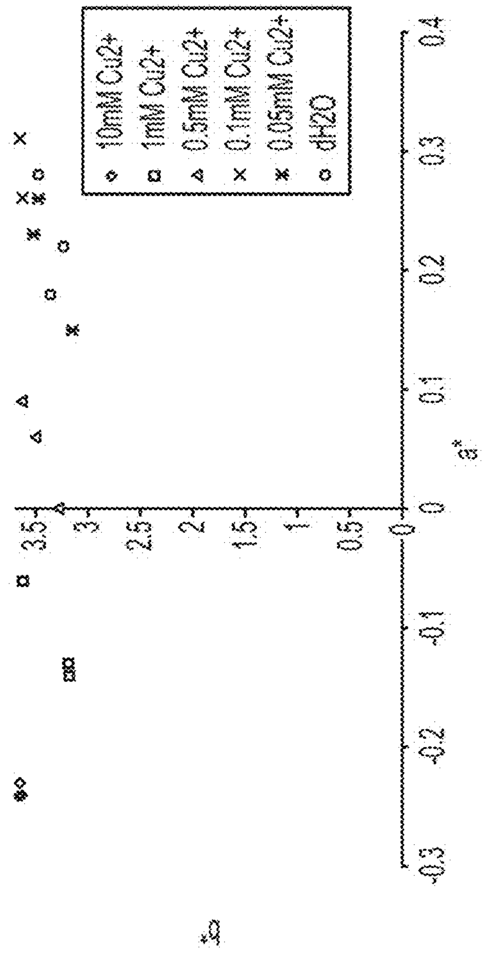
FIG. 10 shows a* vs b* plot of cysteine-functionalized SAMPLE 2 toner deposited at 1 mg/cm$^2$ dipped in various concentrations of $CuSO_4$.
Figure 11:
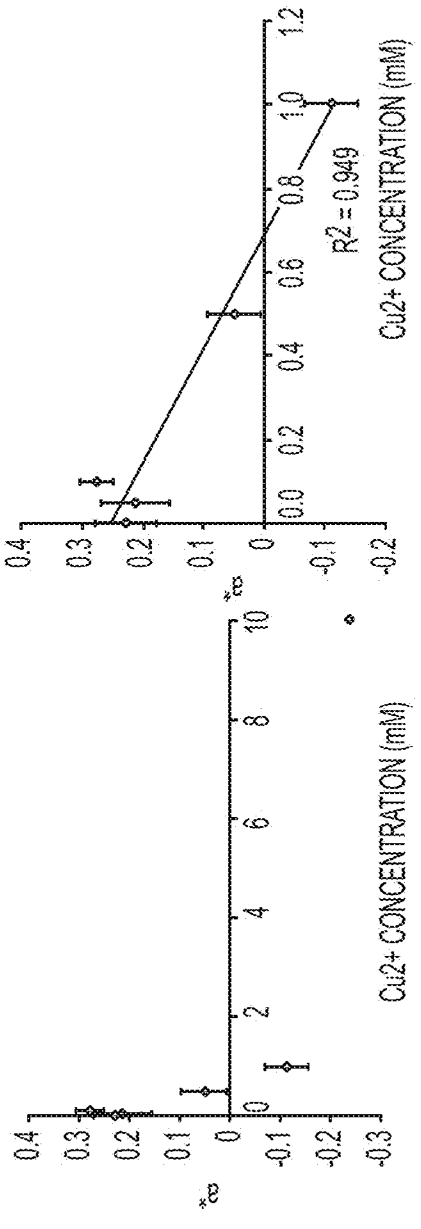
FIG. 11 shows plots of a* values vs. $Cu^{2+}$ concentration over the full range of concentrations tested (left) and from 0 to 1.0 mM $Cu^{2+}$ (right) where the a* values show a linear trend. $R^2$ in the right graph is 0.949.

The a* vs b* values of the 1 mg/$cm^2$ filters are plotted in FIG. 10. The b* values are consistent with varying concentrations of $Cu^{2+}$ whereas the a* values show a clear downward trend with increasing concentrations of $Cu^{2+}$. This trend is plotted in FIG. 11 where the a* values curve downwards with increasing $Cu^{2+}$. The trend appears to be linear at concentrations below 1 mM and it plateaus between 1 mM and 10 mM. The $R^2$ value of the trendline plotted for the values from 0 to 1 mM $Cu^{2+}$ is 0.949, confirming a strong linear relationship between a* values and $Cu^{2+}$ concentration.

Figure 12:
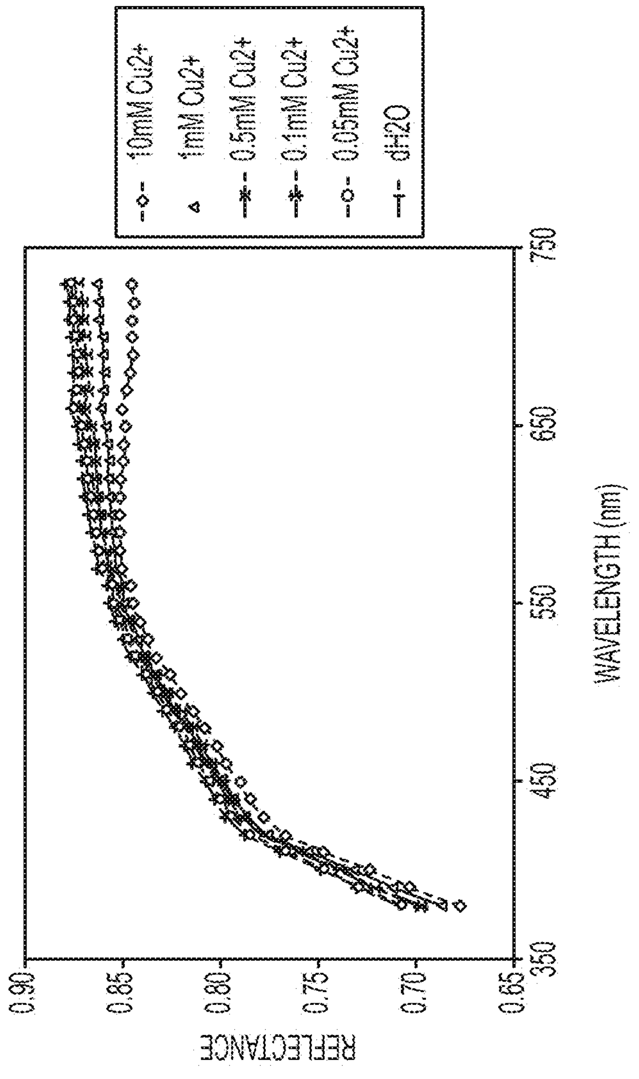
FIG. 12 shows spectrum reflectance values for different concentrations of $Cu^{2+}$.
Figure 13A:
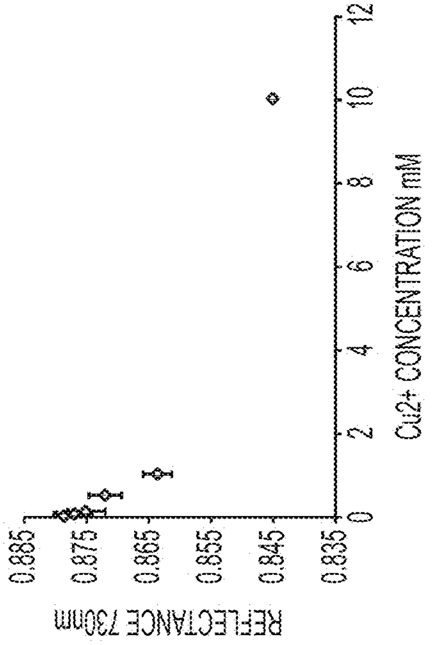
FIGS. 13A, 13B show plots of reflectance at 730 nm values vs. $Cu^{2+}$ concentration over FIG. 13A the full range of concentrations tested and FIG. 13B from 0 to 1.0 mM $Cu^{2+}$ where the reflectance values show a linear trend. $R^2$ in FIG. 13B is 0.9733.
Figure 13B:
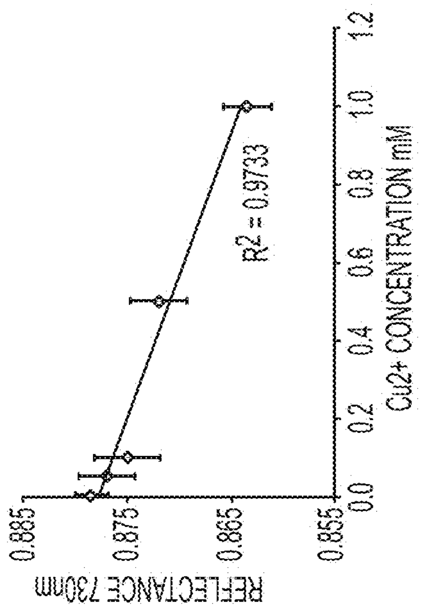

The spectrum reflectance curves of the 1 mg/$cm^2$ filters from 380 nm and 730 nm are plotted in FIG. 12. The curves are well aligned at wavelengths lower than 550 nm. Beyond this point they begin to diverge based on $Cu^{2+}$ concentration. The reflectance at the highest wavelength measured, 730 nm, is plotted in FIG. 13 where, like the a* values, the reflectance curves downwards with increasing $Cu^{2+}$. This trend also appears to be linear at concentrations below 1 mM and plateaus between 1 mM and 10 mM. The $R^2$ value of the trendline plotted for the values from 0 to 1 mM $Cu^{2+}$ is 0.9733, confirming a strong linear relationship between reflectance at 730 nm and $Cu^{2+}$ concentration.

What is claimed is:

1. A detection strip comprising:
a substrate;
a toner composite material fused on the substrate; the toner composite material comprising:
toner particles comprising a sulfonated polyester; and
silver nanoparticles disposed on the surface of the toner particle; and
a ligand covalently linked to the surface of the silver nanoparticles via a thiol, carboxylate, or amine functional group, the ligand selected to detect a target analyte.

2. The detection strip of claim 1, configured with multiple ligands that are spatially addressed, thereby allowing for simultaneous detection of multiple target analytes.

3. The detection strip of claim 1, wherein the substrate is paper.

* * * * *